United States Patent [19]

Slaughter

[11] Patent Number: 4,781,697

[45] Date of Patent: Nov. 1, 1988

[54] REMOVABLE PROTECTIVE SHIELD FOR NEEDLE SHEATH

[76] Inventor: Robert Slaughter, P.O. Box 6272, Carmel, Calif. 93921

[21] Appl. No.: 128,596

[22] Filed: Dec. 4, 1987

[51] Int. Cl.$^4$ .............................................. A61M 5/32
[52] U.S. Cl. ..................................... 604/192; 604/263
[58] Field of Search .......................... 604/192, 187, 263

[56] References Cited

U.S. PATENT DOCUMENTS 4,654,034 4/1987 Masters et al. ...................... 604/192

FOREIGN PATENT DOCUMENTS 8503006 7/1985 PCT Int'l Appl. ................. 604/192

Primary Examiner—John D. Yasko
Attorney, Agent, or Firm—Schroeder, Davis & Orliss Inc.

[57] ABSTRACT

A protective shield device for use with medical apparatus and instruments, namely syringes, hypodermic needles and the like, comprising a removable shield which fits snugly over a needle sheath near its open end and extends radially outward and upward to prevent injury to the fingers and hand when a needle is being inserted into the sheath is described. For a double-ended needle and sheath assemble, a pair of shields coupled together with a flexible tether is provided.

14 Claims, 5 Drawing Sheets

REMOVABLE PROTECTIVE SHIELD FOR NEEDLE SHEATH

BACKGROUND OF THE INVENTION

The present invention relates generally to protective shields for use in the medical field for the purpose of protecting the hand of the user when inserting a needle into its sheath, and, more particularly to a removable and reusable protective shield which slideably fits on the needle receiving container.

Infection and accidental injury due to contact with unsanitary medical equipment, particularly puncture-type wounds from hypodermic needles, have long posed a danger to medical personnel handling such equipment. Accidental needle sticks present the most serious problem because of the high risk of transmitting contagious diseases, including hepatitis, venereal diseases and, of most recent concern, acquired immune deficiency syndrome—shortened to the chilling acronym AIDS.

Hypodermic needles, for example those used for injections or for taking blood samples, are usually equipped with a removable, elongated plastic hollow cap or tube closed at one end which is slipped over the needle and fits snugly on the tapered end of the barrel when a syringe is first assembled that protects and helps keep the needle sterile. The cap is typically replaceable to cover the used, contaminated needle and prevent accidental needlesticks. However, the majority of accidental needle sticks occur during recapping of the needle. Since the bore of the needle cap is dimensionally not much larger than the diameter of the needle, misalignment of the needle with respect to the cap when attempting to insert the needle into the cap results in needlesticks to the hand holding the cap. Eliminating recapping of the needles will not solve the problem as a great number of accidental needlesticks are caused by uncapped needles found in beds, on the floor or in trash containers.

It is well-known in the prior art to provide the needle/syringe with a protective cap device having a radially extending flange near the open end of the cap or to provide a protective cap having a funnel-shaped receiving end to protect the user's hand during recapping. Examples of such protective cap devices are disclosed in U.S. Pat. No. 4,654,034 issued to Edwin J. Masters et al for "SAFETY NEEDLE CAP"; U.S. Pat. No. 4,610,667 issued to James J. Pedicano et al for "DISPOSABLE SAFETY NEEDLE SHEATH"; U.S. Pat No. 4,559,042 issued to Thomas W. Votel for "SAFETY ENCLOSURE FOR DISPOSABLE HYPODERMIC SYRINGE NEEDLE"; and U.S. Pat. No. 4,629,453 issued to Tim M. Cooper for "HYPODERMIC NEEDLE PROTECTIVE DEVICE".

SUMMARY OF THE INVENTION

The present invention provides a removable protective shield which fits snugly over a needle sheath near its open end and extends radially outward and upward to form a flange which protects the fingers and hand when the needle is being inserted into the sheath. With the protective shield disposed on the sheath, misalignment between the needle and the bore will cause the needle to more likely strike the flange rather than the hand of the person holding the sheath. The protective shield has an upturned edge forming a lip around the peripheral of the flange to prevent the needle from slipping off the edge after striking the flange.

For a double-ended needle and sheath system having an elongated sheath and a shorter capping sheath, a protective shield is disposed on each sheath near its open end, to provide protection against needle sticks from either end of the double-ended needle. The two protective shields are coupled together by a flexible strap or tether to prevent separation and loss of the system components when the needle is in use.

The protective shield is molded from plastic or other suitable material strong enough to protect against needle puncture but having a degree of resiliency to allow a snug fit over the sheath. Since the protective shield is not slipped onto the sheath until the needle/syringe is ready to be assembled and used, there are no special packaging or shipping requirements to be considered.

The present invention provides a protective shield which is simple to use and economic to construct and is adaptable for use with any of the needle and sheath systems presently in use including disposable syringes and double-ended needles. Further, the protective shield provides a much needed safety feature which greatly reduces the likelihood of accidental needlesticks during use and disposal of hypodermic needles.

BRIEF DESCRIPTION OF THE DRAWINGS

FIG. 4a is a plan view of the large diameter end of the protective shield of the present invention.

FIG. 4b is a side view taken along line 4—4 of the protective shield of FIG. 4a;

DETAILED DESCRIPTION OF THE PREFERRED EMBODIMENT

Figure 1:
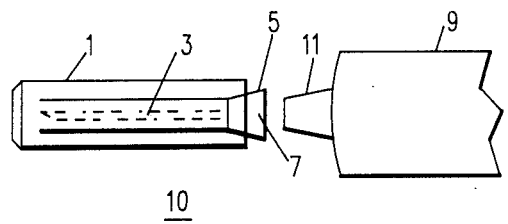
FIG. 1 is a side view of a presently used needle, sheath and syringe end.
Figure 2:
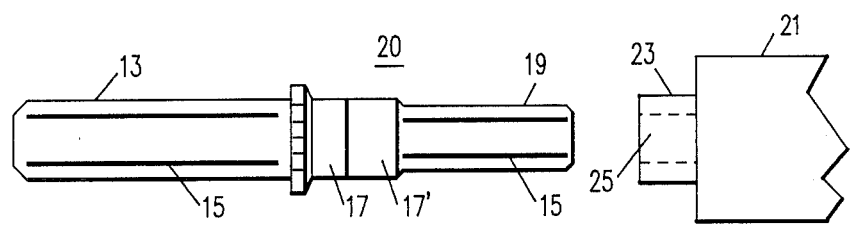
FIG. 2 is a side view of a presently used double-ended needle, sheaths and syringe end.
Figure 3:
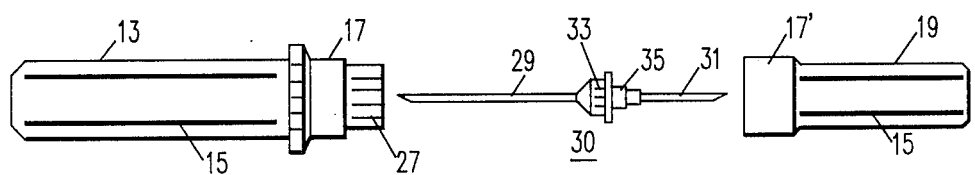
FIG. 3 is an exploded view of the double-ended needle and sheaths of FIG. 2.

Referring initially to FIGS. 1-3, and particularly to FIG. 1, a single needle system 10 and a double-ended needle system 20 will be described. FIG. 1 illustrates a single-ended needle, sheath and syringe commonly in use. Syringe 9 includes tapered tip 11, having a smooth converging outer surface. Single-ended needle 3 is attached to base 5 and is shown inserted in its protective sheath 1. Sheath 1 is closed at one end and open at the other to allow insertion of the needle 3. The sheath 1 may be of constant diameter or it may taper towards the closed end. The sheath 1 may also include a number of equally spaced lengthwise spines 15 (as shown in FIGS. 2 and 3) molded upon the outer surface of the sheath 1. Sheath 1 is in engagement with base 5 such that the sheath 1 is firmly, but removably attached to needle 3 and base 5. Base 5 has a diverging inner surface 7 tapered and sized to permit frictional engagement of base 5 with syringe tip 11. Prior to use of the syringe, the user frictionally engages tip 11 with base 5 to attach the needle 3 to the syringe 9. Sheath 1 is then removed to expose the needle 3 for use. After use, the user reinserts the needle 3 into the sheath 1 for disposal.

Referring now to FIGS. 2 and 3, a double-ended needle and sheath system 20 is shown. Typically, a double-ended needle system includes a syringe 21 having a tip 23 with internal coupling means 25 adapted for engaging the needle hub 35. Needle and sheath assembly 20 includes a long sheath 13 and a short sheath or cap 19 attached to one another by frictional coupling or by a tape or paper label (not shown). Prior to use, short sheath 19 is removed from frictional engagement with end 27 of long sheath 13 thereby exposing short needle 31 and the needle hub 35. Hub 35 is adapted to engage with coupling means 25 of the syringe tip 23. Hub 35 may be either adapted for interference fit with syringe tip 23 or may be externally threaded with syringe tip 23 having corresponding internal threads. Gripping long sheath 13, the user engages hub 35 with coupling means 25 to firmly attach the double-ended needle 30 to the syringe 21. Prior to use of the syringe, long sheath 13 is then removed from frictional engagement with base 33 of long needle 29. After use, the user must enclose the double-ended needle 30 in the sheaths 13 and 19 for disposal. As with the single-ended needle system 10, long needle 29 must be inserted into a relatively small diameter opening in the end 17 of long sheath 13. Then short sheath 19 must be fitted over short needle 31 and frictionally engaged with the end 17 of long sheath 13. The end 17 of long sheath 13 includes a necked down portion 27 having an outer diameter corresponding substantially to the inner diameter of the open end 17' of short sheath 19 such that a tight frictional fit may be afforded. The outer surface of end portion 27 may be roughened or otherwise prepared to enhance frictional engagement with the inner surface of open end 17'. When capping the short needle 31 with the short sheath 19, the user is again faced with inserting the short needle 31 into a relatively small diameter opening in the end 17' of short sheath 19.

Figures 4A, 4B:
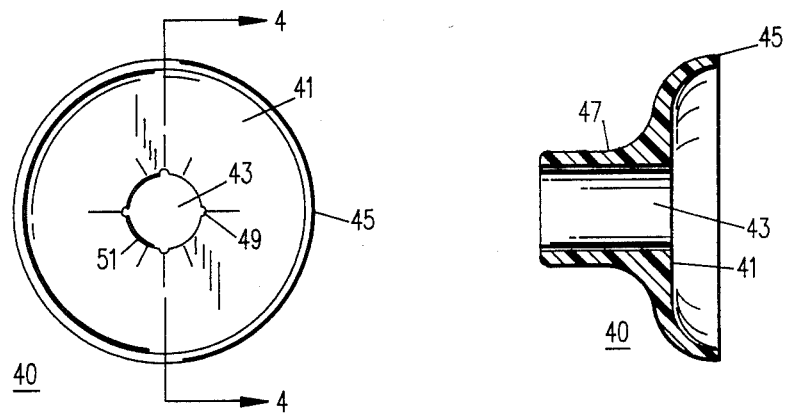
Figure 6:
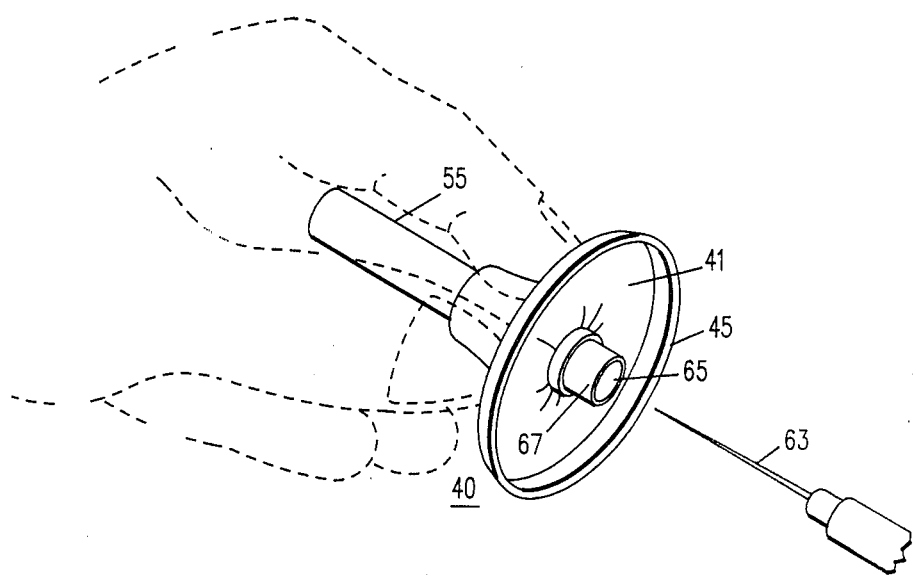
FIG. 6 is a perspective view of the protective shield disposed on a needle sheath.

Referring now to FIGS. 4a and 4b, a protective shield constructed according to the principles of the present invention is shown. Protective shield 40 comprises an annular disc 41 with bore 43 and having an upturned lip 45 about the peripheral of the disc 41. Disc 41 may be planar or may slightly curve upwards in radially directions from the centerline of bore 43 to form a flattened conical or cup-like shape. The closed or backside of the shield 40 is formed into an exterior collar 47 to extend bore 43 and provide structural strength. Exterior collar 47 also provides axial support when disposed on a needle sheath and facilitates gripping the shield with the fingers (as shown in FIG. 6). A number of apertures 49 are spaced about the peripheral 51 of bore 43 for receiving splines 15 (as shown in FIGS. 2 and 3) which are molded upon the outer surface of the needle sheaths provided by some manufacturers.

The protective shield 40 is fabricated from molded plastic or other suitable material. The only requirement is that the material be sufficiently strong to prevent punctures when contacted by a needle. The shield is approximately one and one-half inches in diameter and about a half inch in length. The shields may be manufactured with bores of several different dimensions to accommodate needle sheaths of different sizes. Similarly, shields may be fabricated having different numbers of apertures 49 to accommodate the needle sheaths of different manufacturers.

Figure 5:
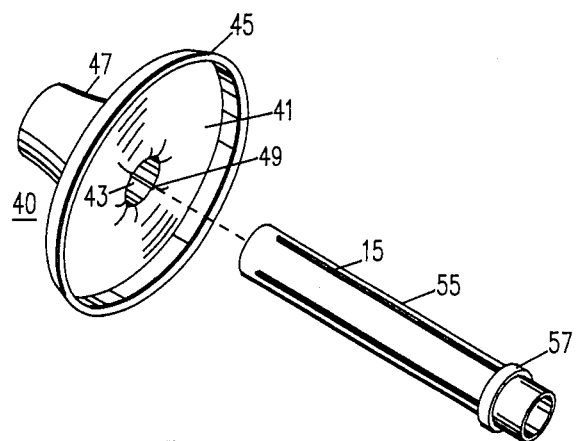
FIG. 5 is a perspective view of the protective shield illustrating the installation on a needle shield.

Referring now also to FIGS. 5 and 6, to install the protective shield 40, the closed end of the needle sheath 55 is inserted into bore 43 and passes through the shield 40 as the shield 40 is slipped on the sheath 55 to the sheath collar 57 with the open end 67 of the sheath protruding slightly from the disc surface 41. The diameter of the bore 43 is substantially the same as the outer diameter of the needle sheath 55 so that a tight frictional fit may be afforded. As the shield 40 is slipped on the sheath 55, the splines 15 engage the spline apertures 49. If the needle 63 is misaligned with the opening 65 when the user attempts to reinsert the needle 63 into the sheath 55, the needle will strike the disc surface 41 of the shield 40 rather than the hand or fingers holding the sheath.

Referring now to FIGS. 2,3,7 and 8, the use of the protective shield with a double-ended needle is illustrated. A pair of shields 71 and 73 are attached to each other by a tether or strap 75. Each shield 71, 73 has corresponding interlocking annular ridges 72B, 72A, respectively, formed around the peripheral of the larger, open end thereof. The pair of shields may be locked together due to the positive engagement of annular ridges 72A and 72B forming a closed clamshell shown in FIG. 8. Upper shield 73 may have a positioning or keying notch 79A which engages with a corresponding protruding key 79B located on the peripheral of the lower shield 71. Prior to disassembling the double-ended needle and sheath assembly, lower shield 71 is first slipped on the long sheath 13 into position. The upper shield 73 (rotated in the direction indicated by arrow 77) is then slipped on the short sheath 19 and gently urged against shield 71 thereby engaging annular ridges 72A and 72B to lock the shields 71, 73 together, rotating the shields 71, 73 slightly, relative to each other, to match up notch 79A with protruding key 79B. The user may now remove the short sheath 19, together with shield 73, exposing the short needle 31 for engagement with the syringe 21. Gently squeezing or compressing slightly and rotating the shields 71,73 relative to one another will disengage the locked annular ridges 72A, 72B. After the needle hub 35 (as shown in FIGS. 2 and 3) has been engaged, the long sheath 13 may be removed to allow use of the needle and syringe. While the needle is in use, the tether or strap 75 prevents the shields 71 and 73 and the associated sheaths 13 and 19, respectively, from becoming separated and misplaced. After use, long needle 29 is reinserted into long sheath 13 and the syringe 21 disengaged from hub 35. The short sheath 19 and shield 73 are now rotated as indicated by arrow 77 to "cap" short needle 31. Any misalignment between the needles and the openings in the open ends of the sheaths 13, 19 will result in the needle striking the protective shields 71 or 73 and not the hand or fingers of the user.

In a second preferred embodiment, bore 74 has counter-bore 76 formed therein forming shoulder 76A. An annular ring or band 78 of brightly colored hard rubber or other suitable resilient material is inserted into counter-bore 76. The outside diameter of band 78 corresponds substantially to the diameter of counter-bore 76 such that a tight frictional fit may be afforded. Alternately, band 78 may be secured within counter-bore 76 with a drop of adhesive 80. When the upper shield 73 is slipped over the short sheath 19, the short sheath 19 is inserted through the band 78. The inner diameter of band 78 is substantially the same as the outer diameter of short sheath 19 such that a tight frictional or interference fit may be achieved. Shoulder 76A ensures that the short sheath 19 will be inserted through band 78 and prevents the band 78 from being forced through the bore 74 by the end 19A of the short sheath 19. Adhesive 80 is of sufficient strength to retain band 78 in position within counter-bore 76 yet will break its bond under the force necessary to insert the short sheath 19 through the band 78. After use, if the upper shield 73 is removed from the short sheath 19, the brightly colored band 78 remains on the short sheath 19 to serve as a warning band that the needle has been used. The band 78 may be bright red or yellow or other suitable color.

Figure 8:
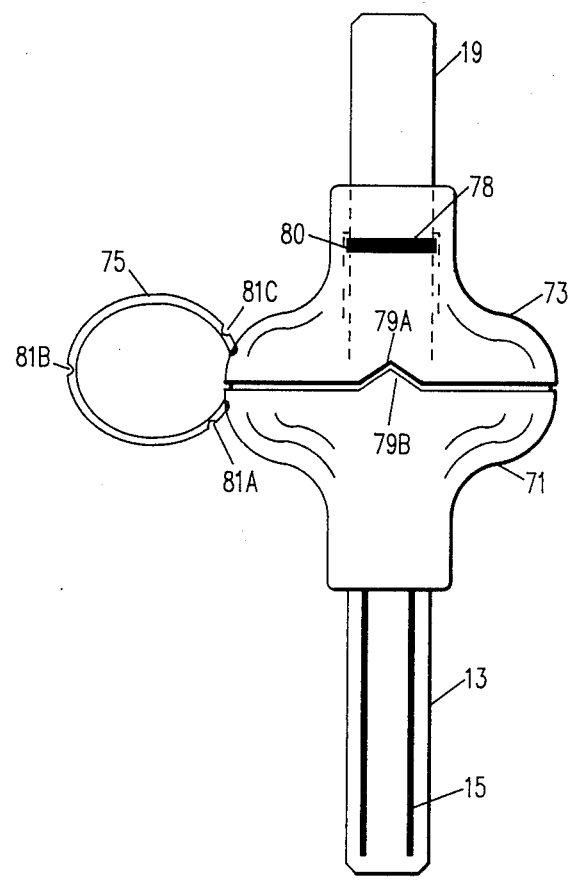
FIG. 8 is a side view of a double-ended needle enclosed in its sheaths with the protective shields installed.
Figure 9:
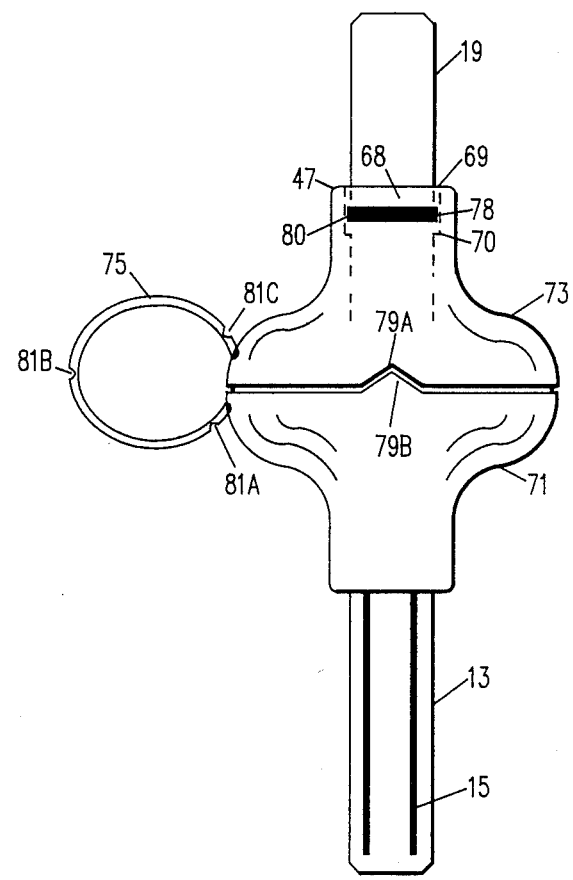
FIG. 9 is a side view of a double-ended needle enclosed in its sheaths with a second embodiment of the protective shields installed.

Referring now also to FIG. 9, the short sheath 19 may have a slightly larger diameter than the long sheath 13 and may be smooth-surfaced rather than having splines 15. In this case, upper shield 73 will have a smooth bore 68 and the shields 71, 73 may be installed on the double-ended needle and sheath assembly while the shields 71, 73 are locked together (as shown in FIGS. 8 and 9). The long, splined sheath 13 is inserted into smooth bore 68 through the upper shield 73 into the lower shield 71, the splines 15 engaging the apertures 49 (as shown in FIG. 5), until the long sheath 13 is seated in the lower shield 71 and the short, smooth-surfaced sheath 19 is inserted into and seated in the upper shield 73. Bore 68 may have counter-bore 69 formed therein and extending from collar 47 partially through the upper shield 73 forming shoulder 70. As described herein above, an annular ring or band 78 is inserted into counter-bore 69 and retained therein by either interference fit or a drop of adhesive 80. The assembled double-ended needle and sheath assembly is inserted into smooth bore 68, the long sheath 13 passes through band 78 and is seated in position in the lower shield 71 and short sheath 19 is inserted through the band 78. Since the inner diameter of band 78 is substantially the same as the outer diameter of short sheath 19, a tight frictional or interference fit is achieved. Shoulder 70 ensures that the band 78 will be tightly seated on short sheath 19 and not be forced through the bore 68. After use of the needle, if the shields 71, 73 are removed from the assembled needle and sheath assembly, the brightly colored band 78 remains on the short sheath 19 to serve as a warning band indicating that the needle has been used.

Alternately, the band 78 may be placed on the short sheath 19 separately, prior to installing the upper and lower shields on the double-ended needle and sheath assembly, then the locked together shields 71, 73 installed as described hereinabove. In this case, the exterior collar 47 serves as a shoulder to prevent the band 78 from being forced through the bore 68, and the counter-bore 69 and shoulder 70 are not required.

Figure 7:
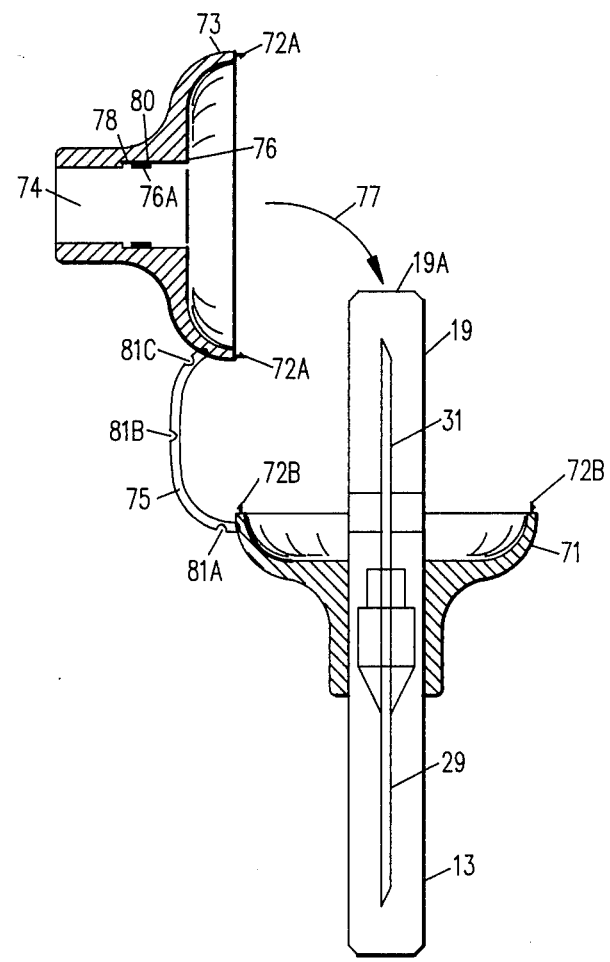
FIG. 7 is a side view of a pair of protective shields disposed on the sheaths for a double-ended needle.

The tether or strap 75 is of sufficient length to allow proper positioning of the shields 71, 73 on the needle sheaths 13, 19, respectively, without disassembling the needle and sheath assembly (as shown in FIGS. 7 and 8). The strap 75 may be made of any material which is sufficiently flexible to allow shields 71 and 73 to move freely relative to each other without becoming disconnected therefrom. The tether or strap 75 may have creases or notches 81A, 81B and 81C formed therein to provide increased yaw or side-to-side flexibility.

It will be understood by those of ordinary skill in the art that the particular embodiments of the invention here presented are by way of illustration only, and that numerous changes and modifications may be made, and the full use of equivalents resorted to, without departing from the spirit or scope of the invention as defined in the accompanying claims.

I claim:

1. A protective shield for use with a two-piece tubular housing having an aperture in the opposing ends of said two-piece tubular housing for receiving and storing a double-ended hypodermic needle, said protective shield comprising:

a pair of shield means, each of said shield means having a centrally disposed bore for sliding said shield means over one piece of said two-piece tubular housing, each of said shield means having an upper side and a lower side, each of said shield means being needle puncture resistant, each of said shield means being removable and cooperatively retained in place with said upper side proximate said aperture, each of said shield means extending radially outward for protecting the hand and fingers from needle puncture; and strap means flexibly attaching each of said shield means to the other shield means such that each of said shield means may move freely relative to the other without becoming disconnected from the other.

2. A protective shield as in claim 1 wherein each of said shield means has an outer edge upwardly protruding from said upper side forming a lip about the outer peripheral of said shield means.

3. A protective shield as in claim 1 wherein each of said shield means has an annular ridge protruding from said upper side about the peripheral thereof, said annular ridge including locking means for locking said pair of shield means together when said pair of shield means are disposed with said upper sides in opposing relationship and each of said shield means is urged into contact with the other thereby engaging said locking means.

4. A protective shield as in claim 1 wherein each of said shield means includes an exterior collar formed on said lower side of said shield means opposite said aperture.

5. A protective shield as in claim 1 wherein each of said shield means has a plurality of spline apertures defined in its inner edge about the peripheral of said centrally disposed bore.

6. A protective shield as in claim 1 wherein the diameter of said centrally disposed bore is substantially the same as the diameter of the associated piece of said two-piece tubular housing such that a tight frictional fit between said shield means and said associated piece may be achieved.

7. A protective shield as in claim 1 wherein one shield means of said pair of shield means includes a centrally disposed counter-bore concentric with said bore and extending from said lower surface partially through said shield means and forming a shoulder, said shield means further including an annular band, said annular band having an outer diameter substantially the same as the diameter of said counter-bore and having an inner diameter substantially the same as the diameter of said bore, said annular band disposed in said counter-bore adjacent said shoulder such that when said shield means is slipped over an associated piece of said two-piece tubular housing said associated piece is inserted through said annular band.

8. A protective shield as in claim 7 wherein said annular band is retained in place within said counter-bore by an adhesive until said associated piece is inserted through said annular band.

9. A protective shield as in claim 7 wherein said annular band is brightly colored.

10. A protective shield as in claim 1 wherein said strap means includes a plurality of notches formed therein.

11. A protective shield as in claim 3 wherein one shield means of said pair of shield means including a locating notch formed in the peripheral thereof, the other shield means of said pair of shield means including locating tab protruding from the peripheral of said other shield means disposed in a corresponding position such that said locating tab engages said locating notch when said pair of shield means are locked together.

12. A protective shield as in claim 1 wherein one shield means of said pair of shield means includes a centrally disposed counter-bore concentric with said bore and extending from said upper surface partially through said shield means and forming a shoulder, said shield means further including an annular band, said annular band having an outer diameter substantially the same as the diameter of said counter-bore and having an inner diameter substantially the same as the diameter of said bore, said annular band disposed in said counter-bore adjacent said shoulder such that when said shield means is slipped over an associated piece of said two-piece tubular housing said associated piece is inserted through said annular band.

13. A protective shield for use with a two-piece tubular housing having an aperture in the opposing ends of said two-piece tubular housing for receiving and storing a double-ended hypodermic needle, said protective shield comprising:

a pair of shield means, each of said shield means having a centrally disposed bore for sliding said shield means over one piece of said two-piece tubular housing, each of said shield means having an upper side and a lower side, each of said shield means being needle puncture resistant, each of said shield means being removable and cooperatively retained in place with said upper side proximate said aperture, each of said shield means extending radially outward for protecting the hand and fingers from needle puncture;

strap means flexibly attaching each of said shield means to the other shield means such that each of said shield means may move freely relative to the other without becoming disconnected from the other; and warning means disposed on one piece of said two-piece tubular housing.

14. A protective shield as in claim 13 wherein said warning means comprises a removable brightly colored resilient annular band, the inner diameter of said annular band substantially the same as the outer diameter of said one-piece of said two-piece tubular housing such that a tight frictional fit between said annular band and said one-piece of said two-piece tubular housing is achieved, said annular band positioned on said one-piece of said two-piece tubular housing prior to sliding said shield means over said two-piece tubular housing and remaining on said one-piece of said two-piece of tubular housing when said shield means is removed.

* * * * *